(12) United States Patent
Li et al.

(10) Patent No.: US 7,405,822 B2
(45) Date of Patent: Jul. 29, 2008

(54) SYSTEMS AND METHODS FOR DETECTION OF RAMAN SCATTERED PHOTONS

(75) Inventors: Zhiyong Li, Redwood City, CA (US); Wei Wu, Mountain View, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/584,020

(22) Filed: Oct. 20, 2006

(65) Prior Publication Data

US 2008/0094620 A1    Apr. 24, 2008

(51) Int. Cl.
*G01J 3/44* (2006.01)
*G01N 21/65* (2006.01)

(52) U.S. Cl. .................................................. 356/301
(58) Field of Classification Search .................. 356/301
See application file for complete search history.

(56) References Cited

U.S. PATENT DOCUMENTS

| 4,575,629 | A | 3/1986 | Schnell et al. | |
|---|---|---|---|---|
| 6,661,547 | B2 | 12/2003 | Kameno et al. | |
| 6,989,897 | B2 | 1/2006 | Chan et al. | |
| 7,022,288 | B1 * | 4/2006 | Boss | 422/82.05 |
| 2006/0164336 | A1 * | 7/2006 | Islam et al. | 356/301 |

OTHER PUBLICATIONS

McPherson, Inc., Spectroscopy Equipment, Detector Summary, 3 pages, http://www.mcphersoninc.com, no date.

Myers Kelley, Anne, "A multimode vibronic treatment of absorption, resonance Raman, and hyper-Rayleigh scattering of excitonically coupled molecular dimmers," J. Chem. Phys., vol. 119, No. 6, pp. 3320-3331, Aug. 8, 2003.

Photonics Industries International, Inc., DC Series, Diode Pumped Solid-State Q-Switched Lasers, 3 pages, no date.

Shoute, Lian C.T., et al., "Tunable resonance hyper-Raman spectroscopy of second-order nonlinear optical chromophores," J. Chem. Phys., vol. 121, No. 15, pp. 7045-7048, Oct. 15, 2004.

Young, Matthew A.., et al., "Surface-enhanced Raman spectroscopy with a laser pointer light source and miniature spectrometer," Can. J. Chem., vol. 82, pp. 1435-1441, 2004.

* cited by examiner

*Primary Examiner*—F. L Evans (57) ABSTRACT

Raman spectroscopy systems include an analyte, a radiation source configured to emit incident radiation having a wavelength, and a detector that is capable of detecting only radiation having wavelengths within a detectable range that includes at least one wavelength corresponding to hyper Raman scattered radiation scattered by the analyte. The wavelength of the incident radiation is outside the detectable range. In particular systems, all wavelengths of radiation that are scattered in the direction of the detector impinge on the detector. Raman spectroscopy methods include providing an analyte and irradiating the analyte with incident radiation having a wavelength, providing a detector capable of detecting only wavelengths of radiation within a detectable range that does not include the wavelength of the incident radiation, and detecting Raman scattered radiation scattered by the analyte. A continuous path free of radiation filters may be provided between the analyte and the detector.

21 Claims, 6 Drawing Sheets

SYSTEMS AND METHODS FOR DETECTION OF RAMAN SCATTERED PHOTONS

FIELD OF THE INVENTION

The present invention relates to Raman Spectroscopy. More particularly, the present invention relates to systems for detecting Raman scattered photons and to methods for detecting and analyzing Raman scattered photons using such systems.

BACKGROUND OF THE INVENTION

Raman spectroscopy is a well-known technique for analyzing molecules or materials. In conventional Raman Spectroscopy, an analyte (or sample) that is to be analyzed is irradiated with high intensity monochromatic radiation provided by a radiation source, such as a laser. A radiation detector detects radiation that is scattered by the analyte. The properties of the scattered radiation provide information relating to the analyte.

Figure 1:
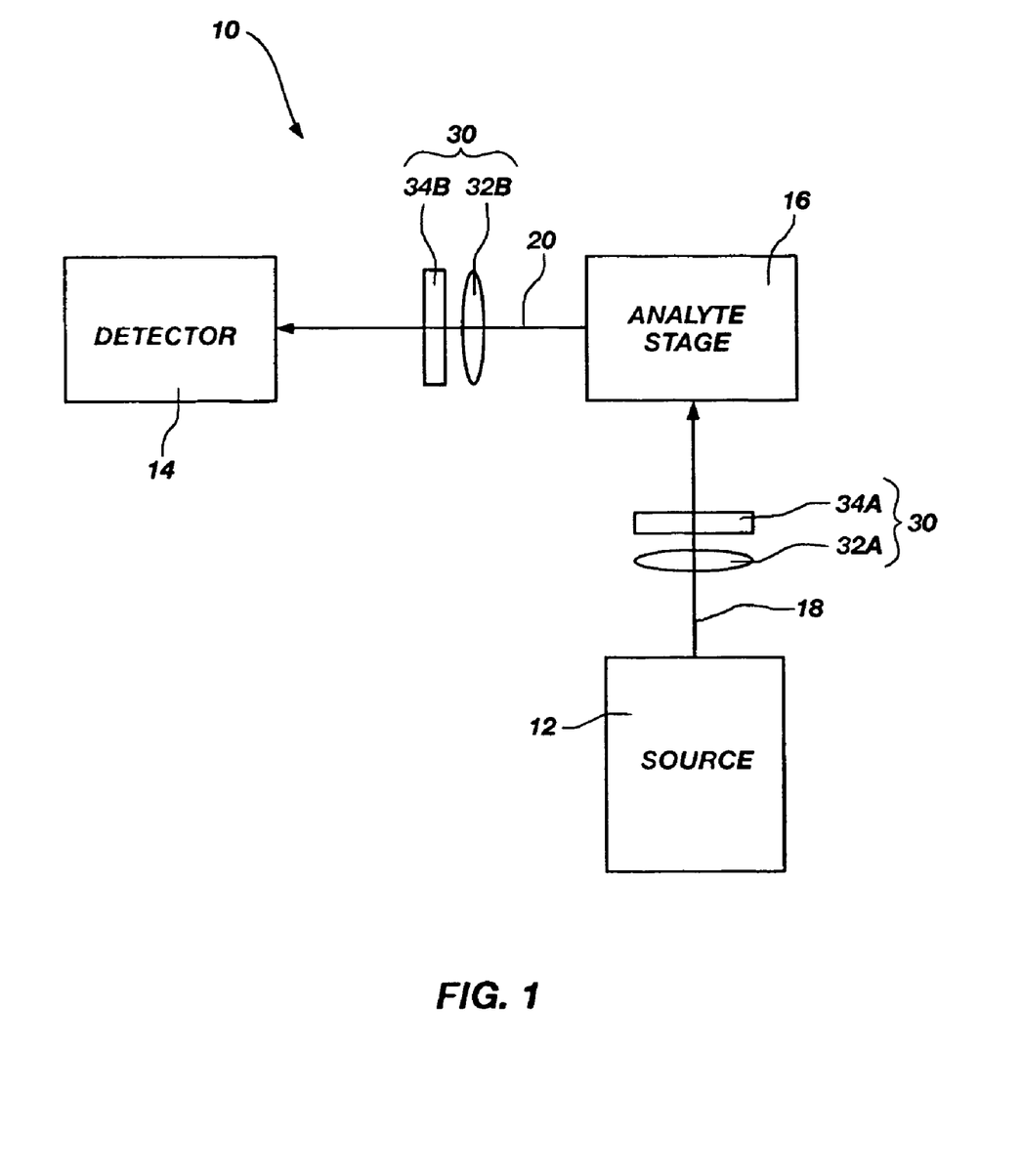
FIG. 1 is a schematic view of a Raman spectroscopy system.

FIG. 1 schematically illustrates a conventional Raman system 10. The Raman spectroscopy system 10 includes an electromagnetic radiation source 12 that is configured to emit incident electromagnetic radiation 18, an analyte stage 16 on which an analyte (not shown in FIG. 1) may be positioned, and an electromagnetic radiation detector 14. The radiation detector 14 is configured to detect at least a portion of scattered radiation 20 that is scattered by the analyte. The Raman spectroscopy system 10 also includes various optical components 30 positioned between the electromagnetic radiation source 12 and the analyte stage 16 (for example, lens 32A and filter 34A), and between the analyte stage 16 and the detector 14 (for example, lens 32B and filter 34B).

The electromagnetic radiation source 12 may be a commercially available laser. The wavelength or wavelengths of incident electromagnetic radiation 18 that may be emitted by the electromagnetic radiation source 12 typically are in the visible region to the near infrared region of the electromagnetic spectrum.

The radiation detector 14 receives and detects at least a portion of the scattered radiation 20 that is scattered by an analyte disposed on the analyte stage 16. The detector 14 may include a device for determining the wavelength of the scattered radiation 20 (for example, a monochromator) and a device for determining the intensity of the scattered radiation 20 (for example, a photomultiplier). Typically, the scattered radiation 20 is scattered in all directions relative to the analyte stage 16.

Optical components 30 positioned between the electromagnetic radiation source 12 and the analyte stage 16 are used to collimate, filter, or focus the incident radiation 18 before the incident radiation 18 impinges on the analyte stage 16. Optical components 30 positioned between the analyte stage 16 and the detector 14 are used to collimate, filter, or focus the scattered radiation 20.

Figure 2:
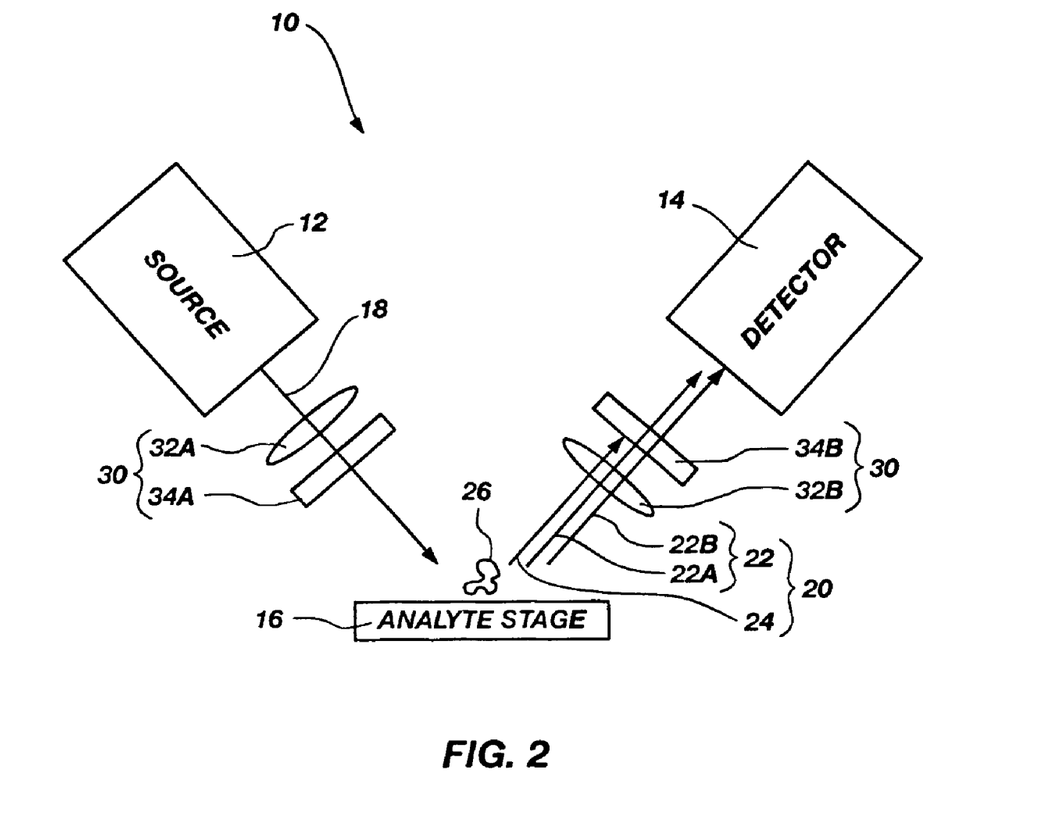
FIG. 2 is side view of the Raman spectroscopy system shown in FIG. 1.

Referring to FIG. 2, an analyte 26 may be provided on the analyte stage 16 of the Raman spectroscopy system 10 (shown in FIG. 1) and irradiated with the incident radiation 18 emitted by the electromagnetic radiation source 12 to perform Raman spectroscopy using the Raman spectroscopy system 10. As the incident radiation 18 impinges on the analyte 26, at least some of the incident radiation 18 will be scattered by the analyte 26. FIG. 2 illustrates scattered radiation 20 that has been scattered by the analyte 26. A majority of the photons of the incident radiation 18 that impinge on the analyte 26 are elastically scattered by the analyte 26. In other words, the scattered photons have the same energy, and thus the same wavelength, as the incident photons. This elastic scattering of photons is termed "Rayleigh scattering," and radiation consisting of these elastically scattered photons is termed "Rayleigh scattered radiation" or "Rayleigh radiation." FIG. 2 also illustrates Rayleigh scattered radiation.

Figure 3:
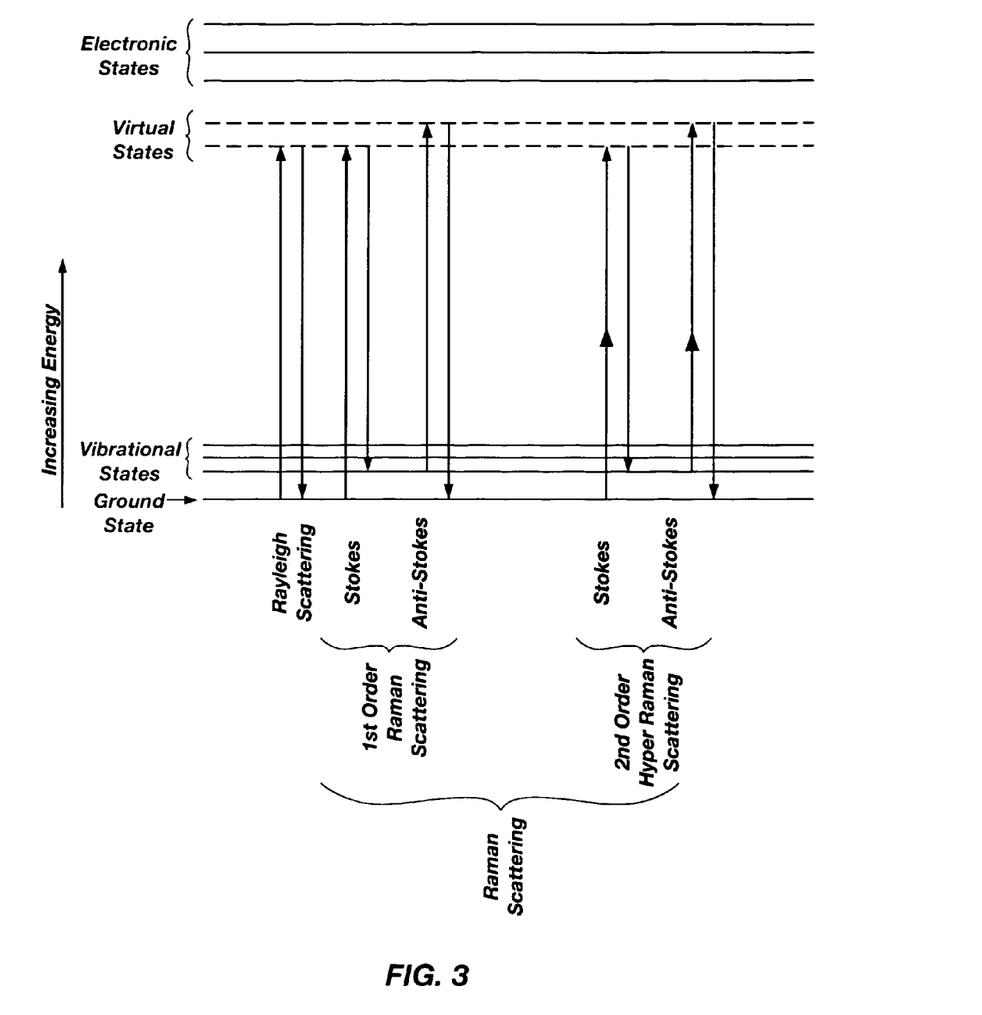
FIG. 3 is a Jablonski energy level diagram schematically representing Rayleigh and Raman scattering processes for a hypothetical analyte.

The Rayleigh scattering process can be further described with reference to the simplified Jablonski diagram shown schematically in FIG. 3, which illustrates various energy levels of a hypothetical analyte, such as the analyte 26 shown in FIG. 2. In FIG. 3, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 3, Rayleigh scattering typically involves absorption of a single photon of the incident radiation 18 by the analyte 26, which causes the analyte 26 to transition from the ground state to a virtual state followed by relaxation to the ground state. As the analyte 26 relaxes to the ground state, the analyte 26 emits a photon of scattered radiation 20 that has energy equal to that of the photon of the incident radiation 18. In this manner, the photon of the incident radiation 18 is considered to have been elastically scattered.

In addition to the Rayleigh scattering of photons, a very small fraction of the photons of the incident radiation 18 may be inelastically scattered by the analyte 26. Referring again to FIG. 2, Raman scattered radiation 22 is also emitted from the analyte 26. Typically, only about 1 in $10^7$ of the photons of the incident radiation 18 is inelastically scattered by the analyte 26. These inelastically scattered photons have a different wavelength than the photons of the incident radiation 18. This inelastic scattering of photons is termed "Raman scattering," and radiation consisting of Raman scattered photons is termed "Raman scattered radiation" or "Raman radiation." The photons of the Raman scattered radiation can have wavelengths less than, or more typically, greater than the wavelength of the photons of the incident radiation 18.

The Raman scattering process can be further described with reference to the simplified Jablonski diagram shown in FIG. 3. When a photon of the incident radiation 18 collides with the analyte 26, energy can be transferred from the photon to the analyte 26, or from the analyte 26 to the photon. When energy is transferred from the photon of the incident radiation 18 to the analyte 26, the Raman scattered photon will have a lower energy and a corresponding longer wavelength than the incident photon. These Raman scattered photons having lower energy than the incident photons are collectively referred to in Raman spectroscopy as the "Stokes radiation." As seen in FIG. 3, 1st order Stokes Raman scattering typically involves absorption of a single photon of the incident radiation 18 by the analyte 26, which causes the analyte 26 to transition from a first energy state (for example, the ground state) to an excited virtual state. The analyte 26 then relaxes to an excited vibrational state of higher energy than the first energy state. As the analyte 26 relaxes to the excited vibrational state, the analyte 26 emits a photon of scattered radiation 20 that has less energy (and a longer wavelength) than the photon of the incident radiation 18. In this manner, the photon of the incident radiation 18 is considered to have been inelastically scattered.

When energy is transferred from the analyte 26 to a photon of the incident radiation 18, the Raman scattered photon will have a higher energy and a corresponding shorter wavelength than the photon of the incident radiation 18. These Raman scattered photons, which have higher energy than the incident photons, are collectively referred to in Raman spectroscopy as the "anti-Stokes radiation." As seen in FIG. 3, 1st order anti-Stokes Raman scattering typically involves absorption of a single photon of the incident radiation 18 by the analyte 26, which causes the analyte 26 to transition from an excited vibrational energy state to an excited virtual state. The analyte 26 then relaxes to a lower energy state (for example, the ground state) than the excited vibrational energy state. As the analyte 26 relaxes to the lower energy state, the analyte 26 emits a photon of scattered radiation 20 that has more energy (and a shorter wavelength) than the photon of the incident radiation 18. In this manner, the photon of the incident radiation 18 is considered to have been inelastically scattered.

The shift in energy (wavelength, frequency, or wave number) of the Raman scattered photons in relation to the Rayleigh scattered photons is known as the "Raman shift."

Raman scattering primarily involves one photon excitation—one photon relaxation process. These Raman scattering processes are often referred to as "1st order" Raman scattering processes. However, multiple photon excitation—single photon relaxation processes are also observed and are referred to as "hyper Raman scattering" processes. Two photon excitation—one photon relaxation scattering processes are referred to as "2nd order" hyper Raman scattering processes, three-photon excitation—one photon relaxation processes are referred to as "3rd order" Raman scattering processes, etc. These higher order Raman scattering processes are often referred to as "harmonics."

In 2nd order scattering processes, a molecule of the analyte 26 in an initial energy state absorbs the energy from two photons of the incident radiation 18 causing an energy transition in the analyte 26 to a virtual excited state, followed by relaxation to a final energy state and emission of a single scattered photon. If the final energy state is the same as the initial energy state, the scattering process is referred to as hyper Raleigh scattering (not represented in FIG. 3). If the final energy state is higher than the initial energy state, the scattering process is referred to as 2nd order Stokes hyper Raman scattering. Finally, if the final energy state is lower than the initial energy state, the scattering process is referred to as 2nd order anti-Stokes hyper Raman scattering. The Stokes and anti-Stokes 2nd order hyper Raman scattering processes are also represented in the Jablonski diagram shown in FIG. 3.

The Raman scattered radiation that is scattered by the analyte 26 (including the hyper Raman scattered radiation) is often referred to as the "Raman signal."

Information may be obtained from hyper Raman scattered radiation that cannot be obtained from 1st order Raman scattered radiation. In particular, vibrational information may be suppressed in Raman scattered radiation due to symmetry issues, thereby resulting in what are often referred to as "silent modes." These silent modes may not be suppressed in the hyper Raman scattered radiation.

Referring again to FIG. 2, when the analyte 26 is irradiated with the incident radiation 18, the scattered radiation 20 may include Raman scattered radiation 22, which may comprise 1st order Raman scattered radiation 22A (Stokes and anti-Stokes) and higher order hyper Raman scattered radiation 22B (Stokes and anti-Stokes), in addition to Rayleigh scattered radiation 24.

The Raman scattered radiation 22 is detected using the radiation detector 14. The wavelengths and corresponding intensity of the Raman scattered radiation 22 may be determined and used to provide a Raman spectral graph. Analytes 26 generate unique Raman spectral graphs. The unique Raman spectral graph obtained by performing Raman spectroscopy can be used to obtain information relating to the analyte 26 including, but not limited to, the identification of an unknown analyte 26, or the determination of physical and chemical characteristics of a known analyte 26.

Raman scattering of photons is a relatively weak process relative to Rayleigh scattering, and hyper Raman scattering is even weaker. Conventional Raman systems are designed primarily to detect 1st order Raman scattered radiation, which has wavelengths proximate the wavelength of the Rayleigh scattered radiation. The detector 14 is capable of detecting the high-intensity Rayleigh scattered radiation 24 in addition to the low-intensity Raman scattered radiation 22. The detection of the Raman scattered radiation 22 may be difficult due to the high intensity of the Rayleigh scattered radiation 24. To overcome this difficulty, the optical components 30 positioned between the analyte stage 16 and the detector 14 include a radiation filter 34B that prevents the Rayleigh scattered radiation 24 from being detected by the detector 14, thus allowing only the Raman scattered radiation 22 to be received by the detector 14. Commercially available notch filters may be used for such purposes. Notch filters are typically very expensive and add to the bulk and fragility of any detector for Raman scattered radiation. As such, eliminating the need for a filter would allow for smaller and cheaper Raman spectroscopy systems. Accordingly, there is a need for Raman spectroscopy systems that may operate without a filter between the analyte 26 and the detector 14.

Surface-enhanced Raman spectroscopy (SERS) is a technique that allows for enhancement of the intensity of the Raman scattered radiation relative to conventional Raman spectroscopy. In SERS, the analyte typically is adsorbed onto or placed adjacent to what is often referred to as a SERS-active structure. SERS-active structures typically include a metal surface or structure. Interactions between the analyte and the metal surface may cause an increase in the intensity of the Raman scattered radiation.

Several types of metallic structures have been employed in SERS techniques to enhance the intensity of Raman scattered radiation that is scattered by an analyte. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing metal nanoparticles, such as nanometer scale needles, particles, and wires, as opposed to a simple roughened metallic surface. This process will be referred to herein as nano-enhanced Raman spectroscopy (NERS). Structures comprising nanoparticles that are used to enhance the intensity of Raman scattered radiation may be referred to as NERS-active structures. The intensity of the Raman scattered radiation that is scattered by an analyte adsorbed on such a NERS-active structure can be increased by factors as high as $10^{16}$.

BRIEF SUMMARY OF THE INVENTION

In one aspect, the present invention includes of a Raman spectroscopy system. The Raman spectroscopy system includes an electromagnetic radiation source, a radiation detector, and an analyte. The electromagnetic radiation source is configured to emit incident radiation having a wavelength. The radiation detector is capable of detecting only electromagnetic radiation having wavelengths within a detectable range of wavelengths that includes at least one wavelength corresponding to hyper Raman scattered radiation scattered by the analyte. The wavelength of the incident radiation is outside the detectable range of wavelengths.

In another aspect, the Raman spectroscopy system includes an electromagnetic radiation source configured to emit incident radiation having a wavelength, a radiation detector configured to detect only electromagnetic radiation having wavelengths within a detectable range of wavelengths, and an analyte positioned to scatter at least some of the incident radiation emitted by the radiation source. The wavelength of the incident radiation is outside the detectable range of wavelengths.

In yet another aspect, the present invention includes a method of detecting Raman scattered radiation. The method includes providing an analyte and irradiating the analyte with incident electromagnetic radiation having a wavelength. A radiation detector is provided that is capable of detecting only electromagnetic radiation having wavelengths within a detectable range of wavelengths. The wavelength of the incident electromagnetic radiation is outside the detectable range of wavelengths. Raman scattered radiation that is scattered by the analyte is detected using the radiation detector.

In a further aspect, the present invention includes a method for collecting information relating to an analyte. The method includes providing an electromagnetic radiation source configured to emit incident electromagnetic radiation having a wavelength, and providing a radiation detector capable of detecting only electromagnetic radiation having wavelengths within a detectable range of wavelengths. The wavelength of the incident electromagnetic radiation is outside the detectable range of wavelengths. The method further includes providing an analyte, providing a continuous path between the analyte and the radiation detector that is free of electromagnetic radiation filters, and irradiating the analyte with the incident electromagnetic radiation. Raman scattered radiation that is scattered by the analyte is detected using the radiation detector.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The term "analyte" as used herein means any molecule, molecules, material, substance, or matter that is to be analyzed by Raman spectroscopy.

The term "nanoparticle" as used herein means a particle of any shape having cross-sectional dimensions of less than about 100 nanometers. Examples of nanoparticles include, but are not limited to, nanodots (including quantum dots), nanowires, nanolines, nanocolumns, and nanospheres.

The term "Raman-enhancing material" as used herein means a material that, when formed into appropriate geometries or configurations, is capable of increasing the number of Raman scattered photons that are scattered by an analyte when the analyte is located proximate to that material, and the analyte and material are subjected to electromagnetic radiation. Raman-enhancing materials include, but are not limited to, silver, gold, and copper. Raman-enhancing materials are used to form SERS-active structures and NERS-active structures.

The term "Raman-enhancing structure" as used herein means a structure that is capable of increasing the number of Raman scattered photons that are scattered by an analyte when the analyte is located proximate to the structure and the analyte and structure are subjected to electromagnetic radiation. Raman-enhancing structures include SERS-active structures and NERS-active structures.

The illustrations presented herein are not meant to be actual views of any particular Raman-enhancing structure or Raman spectroscopy system, but are merely idealized representations, which are employed to describe the present invention. Additionally, elements common between figures may retain the same numerical designation.

Figure 4:
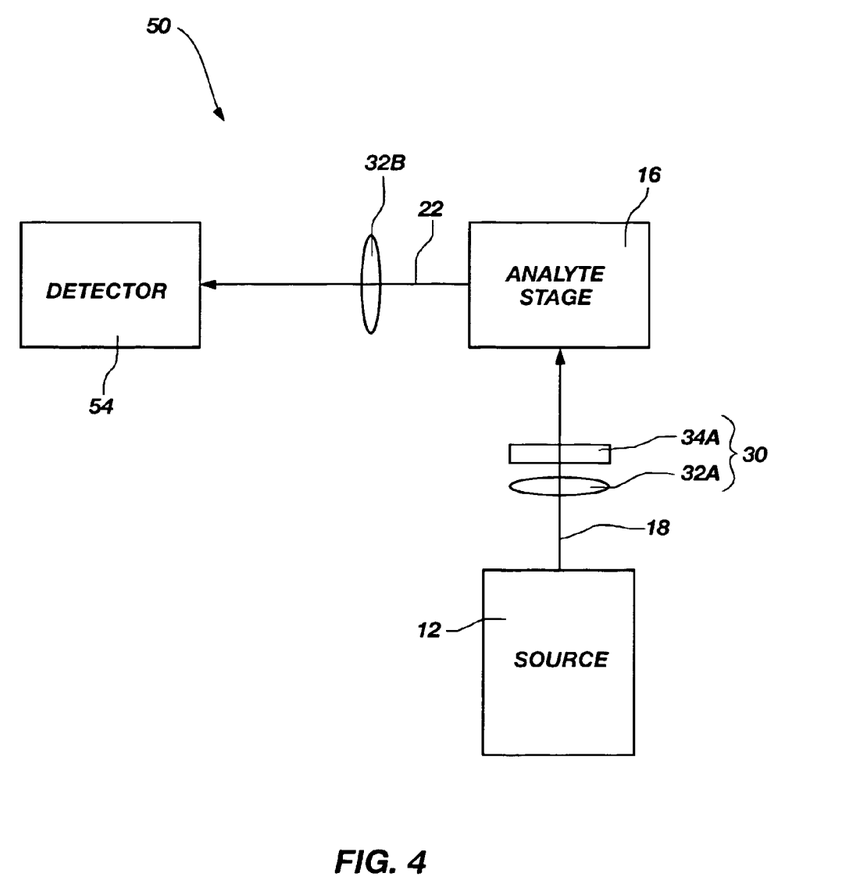
FIG. 4 is a schematic diagram of a representative embodiment of a Raman spectroscopy system of the present invention.

FIG. 4 illustrates a representative Raman spectroscopy system 50 that embodies teachings of the present invention. The Raman spectroscopy system 50 includes an electromagnetic radiation source 12, an analyte stage 16, and an electromagnetic radiation detector 54. The electromagnetic radiation source 12 is configured to emit incident radiation 18 having a selected wavelength. The electromagnetic radiation detector 54 is capable of detecting only electromagnetic radiation having wavelengths within a detectable range of wavelengths. The wavelength of the incident radiation 18 emitted by the electromagnetic radiation source 12 is outside the detectable range of wavelengths of the radiation detector 54.

In this configuration, a radiation filter (such as radiation filter 34B shown in FIGS. 1-2) is not needed between the analyte stage 16 and the electromagnetic radiation detector 54 for purposes of filtering out Rayleigh scattered radiation, since the Rayleigh scattered radiation has the same wavelength as the incident radiation 18 and is not detectable by the electromagnetic radiation detector 54. The electromagnetic radiation detector 54, by design, will not detect any radiation that has a wavelength equal to the wavelength of the incident radiation 18 and impinges on the electromagnetic radiation detector 54. In this configuration, the electromagnetic radiation detector 54 cannot detect the incident radiation 18 or Rayleigh scattered radiation. The electromagnetic radiation detector 54 may be limited to detecting Raman scattered radiation 22 that has a longer wavelength than the incident radiation 18, limited to detecting Raman scattered radiation 22 that has a shorter wavelength than the incident radiation 18, or both. In this configuration, a continuous path for scattered radiation may be provided through the space between the analyte stage 16 and the radiation detector 54 that is free of electromagnetic radiation filters.

The Raman spectroscopy system 50 may also include various optical components 30 (such as, for example, lens 32A and filter 34A) positioned between the electromagnetic radiation source 12 and the analyte stage 16. These optical components 30 may be used to collimate, filter, or focus the incident radiation 18 before the incident radiation 18 impinges on the analyte stage 16. Alternatively, the incident radiation 18 that is emitted by the electromagnetic radiation source 12 may be delivered directly from the electromagnetic radiation source 12 to the analyte stage 16. Furthermore, the Raman spectroscopy system 50 may include optical components 30 (such as, for example, lens 32B) other than radiation filters configured to filter particular wavelengths of scattered radiation between the analyte stage 16 and the radiation detector 54.

The electromagnetic radiation source 12 may include any suitable source for emitting incident radiation 18 at a desired wavelength, and may be capable of emitting a tunable wavelength of incident radiation 18. For example, commercially available semiconductor lasers, helium-neon lasers, carbon dioxide lasers, light emitting diodes, incandescent lamps, and many other known radiation emitting sources may be used as the radiation source 12. The wavelengths that are emitted by the electromagnetic radiation source 12 may be within or near the visible region of the electromagnetic spectrum.

The incident radiation 18 may be transferred from the electromagnetic radiation source 12 to the analyte stage 16 using optical fibers. In addition, Raman scattered radiation 22 may be transferred from the analyte stage 16 to the electromagnetic radiation detector 54 using optical fibers.

The electromagnetic radiation detector 54 receives and detects the photons of the Raman scattered radiation 22. The electromagnetic radiation detector 54 may include a device for determining the wavelength of the Raman scattered radiation 22 (for example, a monochromator) and a device for determining the intensity of the Raman scattered radiation 22 (for example, a photomultiplier).

The Raman scattered radiation 22 includes 1st order Raman scattered radiation 22A (FIG. 2) and higher order hyper Raman scattered radiation (22B). It should be understood that Rayleigh scattered radiation 24 (FIG. 2) impinges on the electromagnetic radiation detector 54 even though the Rayleigh scattered radiation 24 is not detectable by the radiation detector 54. Furthermore, the electromagnetic radiation detector 54 may be capable of detecting both 1st order Raman scattered radiation and higher order hyper Raman scattered radiation. Alternatively, the detectable range of wavelengths may not include the 1st order Raman scattered radiation and the electromagnetic radiation detector 54 may be capable of detecting only higher order hyper Raman scattered radiation.

Hyper-Raman radiation typically utilizes near-IR excitation, which is not in resonance with most molecular eletronic transitions. This can eliminate any potential fluorescence problem that may exist in the Vis-excited Raman. Additionally, any potential photochemical damage to molecules that may occur under UV-Vis excitation can be eliminated. Additionally, near-IR excitation falls into the so-called "biological window," namely about 700 to about 1400 nm range, where most biological material is transparent. Therefore, using near-IR excitation can facilitate study of biological systems such as, for example, by penetrating skin and exciting the Raman scattering without any incidence of radiation blockage.

Typically, photons of the Raman scattered radiation 22 are scattered in all directions relative to the analyte stage 16. Thus, the position of the electromagnetic radiation detector 54 relative to the analyte stage 16 is not particularly important.

In one embodiment of the present invention, the electromagnetic radiation source 12 may be an infrared laser that is configured to emit infrared radiation at a selected wavelength of 1064 nanometers. Such a detector is commercially available from, for example, Photonics Industries International Inc. of Bohemia, N.Y. Furthermore, the electromagnetic radiation detector 54 may be capable of detecting only electromagnetic radiation having wavelengths less than about 1000 nanometers. For example, the electromagnetic radiation detector 54 may be capable of detecting only electromagnetic radiation having wavelengths within a detectable range of wavelengths extending from about 30 nanometers to about 900 nanometers. Alternatively, the electromagnetic radiation detector 54 may be capable of detecting only electromagnetic radiation having wavelengths within a detectable range of wavelengths extending from about 110 nanometers to about 800 nanometers. Such electromagnetic radiation detectors are commercially available from, for example, McPherson Inc. of Chelmsford, Mass.

Figure 5:
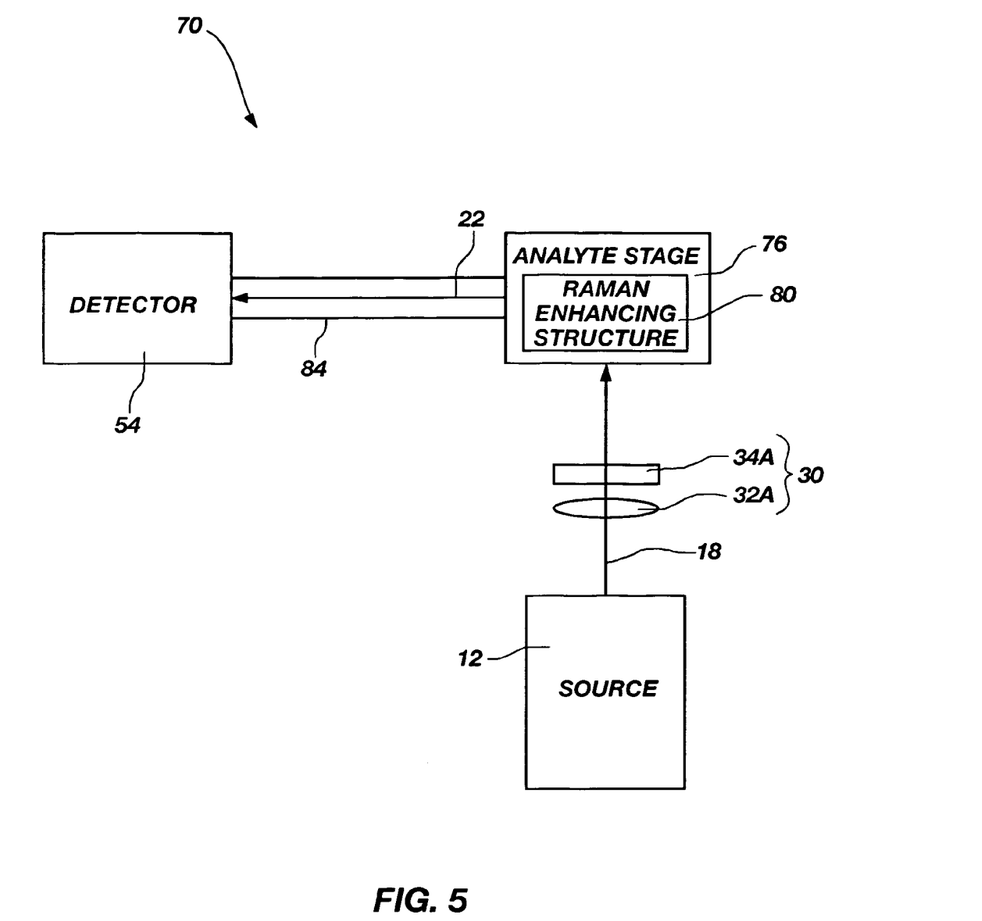
FIG. 5 is a schematic diagram of a another representative embodiment of a particular Raman spectroscopy system of the present invention.

FIG. 5 illustrates another representative Raman spectroscopy system 70 that embodies teachings of the present invention. The Raman spectroscopy system 70 includes an electromagnetic radiation source 12, an analyte stage 76, and an electromagnetic radiation detector 54, as previously described in relation to the Raman spectroscopy system 50 shown in FIG. 4. The Raman spectroscopy system 70 also may include various optical components 30 (such as, for example, lens 32A and filter 34A) positioned between the electromagnetic radiation source 12 and the analyte stage 76. These optical components 30 may be used to collimate, filter, or focus the incident radiation 18 before the incident radiation 18 impinges on the analyte stage 76.

The Raman spectroscopy system 70 may include a fiber optic cable 84 that is configured to transmit Raman scattered radiation 22 from the analyte stage 76 to the electromagnetic radiation detector 54. In this configuration, a continuous path for scattered radiation is provided between the analyte stage 76 and the radiation detector 54 through the fiber optic cable 84 that is free of electromagnetic radiation filters.

The analyte stage 76 of the Raman spectroscopy system 70 may include a Raman-enhancing structure 80, which may be used to enhance the intensity of the Raman scattered radiation 22 (including the intensity of hyper Raman scattered radiation). For example, the Raman-enhancing structure 80 may include a simple roughened surface of a Raman-enhancing material (such as, for example, gold, silver, or copper). Alternatively, the Raman-enhancing structure 80 may include randomly or selectively oriented nanoparticles of a Raman-enhancing material. The Raman-enhancing structure 80 may be configured to enhance the intensity of the Raman scattered radiation 22 that is scattered by an analyte (not shown) when the analyte is provided proximate the Raman-enhancing structure 80, and when the analyte and the Raman-enhancing structure 80 are irradiated with the incident radiation 18.

Figure 6:
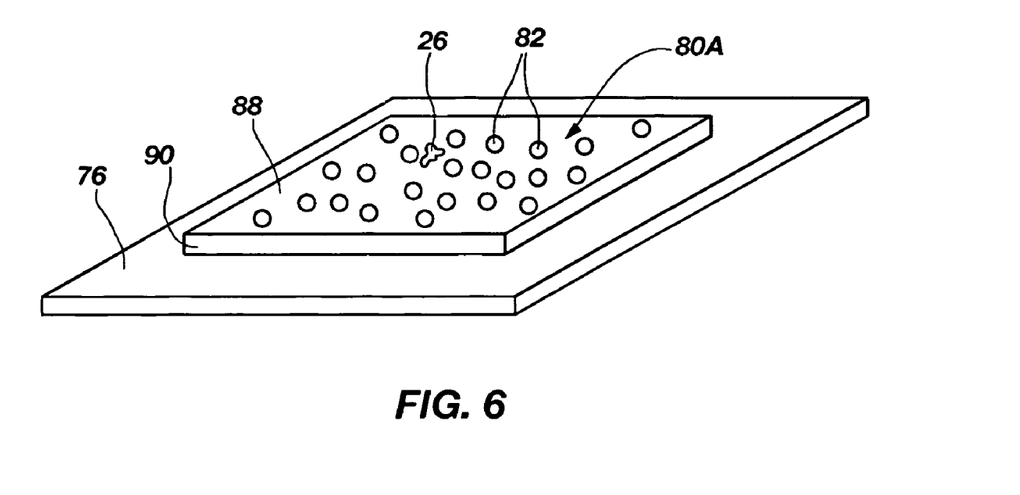
FIGS. 6-7 are perspective views of representative Raman-enhancing structures that can be used in Raman spectroscopy systems of the present invention.

FIG. 6 depicts the analyte stage 76 and a representative Raman-enhancing structure 80A, which may be used in the Raman spectroscopy system 70 shown in FIG. 5. The Raman-enhancing structure 80A may include a plurality of silver nanospheres 82 randomly dispersed on a surface 88 of a dielectric substrate 90. In this configuration, an analyte 26 may be provided on the Raman-enhancing structure 80A proximate at least two of the nanospheres 82. The analyte 26 and the nanospheres 82 may then be irradiated with incident radiation 18 emitted by the electromagnetic radiation source 12 (shown in FIG. 5). The nanospheres 82 may enhance the intensity of Raman scattered radiation 22 (including hyper Raman scattered radiation) scattered by the analyte 26 when the analyte 26 and the nanospheres 82 are irradiated with the incident radiation 18. Alternatively, the nanospheres 82 may be dispersed as an ordered array.

The Raman-enhancing structure 80A may be provided using a commercially available dielectric substrate 90 and commercially available silver nanospheres 82. For example, the silver nanospheres 82 may be suspended in a liquid, and the liquid suspension may then be dispersed over the surface 88 of the substrate 90 and allowed to dry, leaving behind the nanospheres 82 on the surface 88 of the substrate 90.

Figure 7:
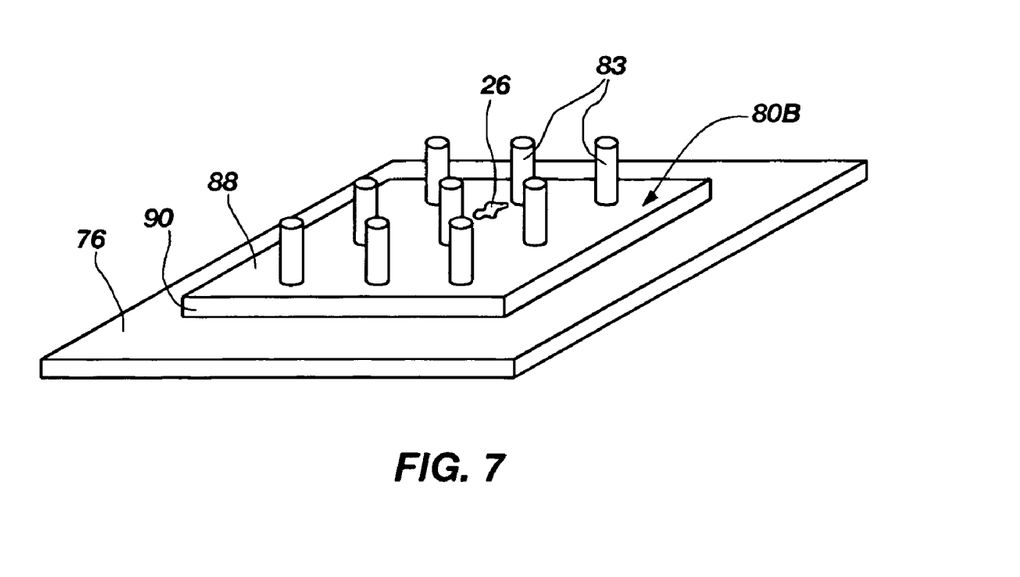

FIG. 7 depicts the analyte stage 76 and another representative Raman-enhancing structure 80B, which may be used in the Raman spectroscopy system 70 shown in FIG. 5. The Raman-enhancing structure 80B may include a plurality of gold nanocolumns 83 selectively dispersed on the surface 88 of the substrate 90 in an ordered array. In this configuration, an analyte 26 may be provided on the Raman-enhancing structure 80B proximate at least two of the nanocolumns 83. The analyte 26 and the nanocolumns 83 may then be irradiated with incident radiation 18 emitted by the electromagnetic radiation source 12 (shown in FIG. 5). The nanocolumns 83 may enhance the intensity of Raman scattered radiation 22 (including hyper Raman scattered radiation) scattered by the analyte 26 when the analyte 26 and the nanocolumns 83 are irradiated with the incident radiation 18.

The Raman-enhancing structure 80B may be fabricated lithographically using techniques known in the art of microdevice and nanodevice fabrication. For example, a commercially available dielectric substrate 90 may be provided. A layer of Raman-enhancing material may then be provided on the surface 88 of the substrate 90 by, for example, physical vapor deposition. The layer of Raman-enhancing material may then be selectively etched, leaving behind the nanocolumns 83 of Raman-enhancing material.

Raman spectroscopy systems that embody teachings of the present invention (such as, for example, the Raman spectroscopy system 50 shown in FIG. 4 and the Raman spectroscopy system 70 shown in FIG. 5) may be used to perform Raman spectroscopy on an analyte. In particular, such systems may be used to detect Raman scattered radiation and to collect information relating to an analyte from the Raman scattered radiation.

For example, an analyte may be provided and irradiated with incident electromagnetic radiation. The electromagnetic radiation may have a particular, selected wavelength. For example, the analyte may be irradiated with incident radiation 18 using the previously described electromagnetic radiation source 12, which may be a laser. An electromagnetic radiation detector is provided that is capable of detecting only electromagnetic radiation having wavelengths within a detectable range of wavelengths. The detectable range of wavelengths may be a continuous range of wavelengths. The wavelength of the incident radiation is outside the detectable range of wavelengths. Furthermore, the detectable range of wavelengths may include at least one wavelength corresponding to hyper Raman scattered radiation that is scattered by the analyte. As an example, the electromagnetic radiation detector may be the previously described radiation detector 54 shown in FIGS. 4-5.

In one particular method according to the present invention, the detectable range of wavelengths of the radiation detector may include only higher order hyper Raman scattered radiation that is scattered by the analyte, and may not include the first order Raman scattered radiation that is scattered by the analyte. In other words, the first order Raman scattered radiation may consist of wavelengths of radiation outside the detectable range of wavelengths of the radiation detector, while higher order Raman scattered radiation may comprise at least one wavelength within the detectable range of wavelengths.

Because the radiation detector is not capable of detecting electromagnetic radiation having a wavelength equal to the wavelength of the incident radiation, a radiation filter is not needed to remove such radiation from the scattered radiation that impinges on the radiation detector. Therefore, a continuous path for all scattered radiation that is scattered by the analyte (including Rayleigh scattered radiation) may be provided between the analyte and the radiation detector that is free of electromagnetic radiation filters. The continuous path may simply be provided by a space between the analyte and the radiation detector. Alternatively, a fiber optic cable may provide a continuous path for scattered radiation between the analyte and the radiation detector.

The intensity of the Raman scattered radiation (including hyper Raman scattered radiation) that is scattered by the analyte may be enhanced by providing a Raman-enhancing structure (such as, for example, the Raman-enhancing structure 80A shown in FIG. 6 or the Raman-enhancing structure 80B shown in FIG. 7), positioning the analyte proximate the Raman-enhancing structure, and irradiating the analyte and the Raman-enhancing structure with incident electromagnetic radiation.

Raman spectroscopy systems that embody teachings of the present invention and methods for performing Raman spectroscopy according to the present invention eliminate the need for radiation filters positioned between an analyte and a radiation detector for purposes of filtering Rayleigh scattered radiation from the scattered radiation that impinges on the radiation detector. Cheaper and smaller Raman spectroscopy systems may be provided by eliminating such radiation filters in accordance to teachings of the present invention. Furthermore, the Raman spectroscopy systems and the methods for performing Raman spectroscopy described herein may be used to facilitate the detection of hyper Raman scattered radiation, as previously described.

Although the foregoing description contains many specifics, these are not to be construed as limiting the scope of the present invention, but merely as providing certain representative embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A Raman spectroscopy system, comprising:
   an electromagnetic radiation source configured to emit incident radiation having a wavelength;
   an analyte; and
   a radiation detector capable of detecting only electromagnetic radiation having wavelengths within a detectable range of wavelengths, wherein the detectable range of wavelengths includes wavelengths corresponding to at least two orders of Raman scattered radiation scattered by the analyte, and wherein the wavelength of the incident radiation is outside the detectable range of wavelengths.

2. The Raman spectroscopy system of claim 1, wherein the electromagnetic radiation source comprises a laser.

3. The Raman spectroscopy system of claim 2, wherein the laser is configured to emit incident radiation having a wavelength of about 1064 nanometers.

4. The Raman spectroscopy system of claim 3, wherein the detectable range of wavelengths includes wavelengths less than about 1000 nanometers.

5. The Raman spectroscopy system of claim 4, where the detectable range of wavelengths extends from about 30 nanometers to about 900 nanometers.

6. The Raman spectroscopy system of claim 5, where the detectable range of wavelengths extends from about 110 nanometers to about 800 nanometers.

7. The Raman spectroscopy system of claim 1, further comprising a Raman-enchancing structure configured to enhance the intensity of Raman scattered radiation scattered by the analyte when the analyte is provided proximate the Raman-enhancing structure and the analyte and the Raman-enhancing structure are irradiated with the incident radiation.

8. A Raman spectroscopy system, comprising:
an electromagnetic radiation source configured to emit incident radiation having a selected wavelength;
an analyte stage; and
a radiation detector configured to detect only electromagnetic radiation having wavelengths within a detectable range of wavelengths, wherein the detectable range of wavelengths includes the wavelengths of at least two orders of Raman scattered radiation, and wherein the wavelength of the incident radiation is outside the detectable range of wavelengths.

9. The Raman spectroscopy system of claim 8, further comprising an analyte positioned on the analyte stage to scatter at least some of the incident radiation emitted by the radiation source.

10. The Raman spectroscopy system of claim 9, wherein Rayleigh scattered radiation and Raman scattered radiation that is scattered by the analyte in the direction of the radiation detector impinges on the radiation detector, the detector being configured to detect at least two orders of Raman scattered radiation, the detector being incapable of detecting Rayleigh scattered radiation.

11. A method of detecting Raman scattered radiation, comprising: providing an analyte;
irradiating the analyte with incident electromagnetic radiation having a selected wavelength;
providing a radiation detector capable of detecting only electromagnetic radiation having wavelengths within a detectable range of wavelengths, wherein the detectable range of wavelengths includes wavelengths of at least two orders of Raman scattered radiation, and wherein the wavelength of the incident electromagnetic radiation is outside the detectable range of wavelengths, and
detecting at least two orders of Raman scattered radiation that is scattered by the analyte using the radiation detector.

12. The method of claim 11, wherein the detectable range of wavelengths does not include first order Raman scattered radiation that is scattered by the analyte.

13. The method of claim 12, wherein irradiating the analyte comprises providing a laser configured to emit the incident electromagnetic radiation.

14. The method of claim 13, wherein the incident electromagnetic radiation has a wavelength of about 1064 nanometers and the detectable range of wavelengths extends from about 30 nanometers to about 900 nanometers.

15. The method of claim 11, further comprising enhancing the Raman scattered radiation that is scattered by the analyte using a Raman-enhancing structure.

16. A method for collecting information relating to an analyte comprising:
providing an analyte;
providing an electromagnetic radiation source configured to emit incident electromagnetic radiation having a wavelength;
providing a radiation detector capable of detecting only electromagnetic radiation having wavelengths within a detectable range of wavelengths, wherein the detectable range of wavelengths includes wavelengths of at least two orders of Raman scattered radiation, and wherein the wavelength of the incident electromagnetic radiation is outside the detectable range of wavelengths;
providing a continuous path between the analyte and the radiation detector, the continuous path being free of electromagnetic radiation filters;
irradiating the analyte with the incident electromagnetic radiation; and
detecting Raman scattered radiation that is scattered by the analyte using the radiation detector.

17. The method of claim 16, wherein detecting Raman scattered radiation comprises detecting at least two orders of hyper Raman scattered radiation that is scattered by the analyte.

18. The method of claim 16 wherein the incident electromagnetic radiation has a wavelength of approximately 1064 nanometers and the detectable range of wavelengths consists of wavelengths in a range from about 30 nanometers to about 900 nanometers.

19. The method of claim 16, wherein providing a continuous path between the analyte and the radiation detector comprises providing a fiber optic cable between the analyte and the radiation detector.

20. The method of claim 16, further comprising enhancing the Raman scattered radiation that is scattered by the analyte using a Raman-enhancing structure.

21. The method of claim 16, wherein first order Raman scattered radiation consists of wavelengths of radiation outside the detectable range of wavelengths, and higher order Raman scattered radiation comprises wavelengths within the detectable range of wavelengths.

\* \* \* \* \*

UNITED STATES PATENT AND TRADEMARK OFFICE
CERTIFICATE OF CORRECTION

| | | |
|---|---|---|
| PATENT NO. | : 7,405,822 B2 | Page 1 of 1 |
| APPLICATION NO. | : 11/584020 | |
| DATED | : July 29, 2008 | |
| INVENTOR(S) | : Zhiyong Li et al. | |

It is certified that error appears in the above-identified patent and that said Letters Patent is hereby corrected as shown below:

On the face page, in field (56), under "U.S. Patent Documents", in column 1, line 5, delete "2006/0164336 A1" and insert -- 2006/0164636 A1 --, therefor.

In column 11, line 14, in Claim 7, delete "Raman-enchancing" and insert -- Raman-enhancing --, therefor.

Signed and Sealed this

Fourteenth Day of July, 2009

JOHN DOLL
*Acting Director of the United States Patent and Trademark Office*